United States Patent [19]

Ikenaka et al.

[11] Patent Number: 4,762,917

[45] Date of Patent: * Aug. 9, 1988

[54] OLIGOSACCHARIDE DERIVATIVES AND THEIR USE AS SUBSTRATE FOR MEASURING α-AMYLASE ACTIVITY

[75] Inventors: Tokuji Ikenaka, Sakai; Kaoru Omichi, Toyonaka, both of Japan

[73] Assignee: Wako Pure Chemical Industries, Ltd., Osaka, Japan

[*] Notice: The portion of the term of this patent subsequent to Sep. 29, 2004 has been disclaimed.

[21] Appl. No.: 765,080

[22] Filed: Aug. 13, 1985

[30] Foreign Application Priority Data

Aug. 24, 1984 [JP] Japan ................. 59-176320

[51] Int. Cl.$^4$ ............................................. C08B 37/00
[52] U.S. Cl. .................................... 536/4.1; 536/17.3
[58] Field of Search ............................ 536/4.1, 17.3

[56] References Cited

U.S. PATENT DOCUMENTS

| | | | |
|---|---|---|---|
| 4,233,403 | 11/1983 | Menson et al. | 435/22 |
| 4,544,631 | 10/1985 | Rauscher et al. | 435/22 |
| 4,622,295 | 11/1986 | Ikenaka et al. | 435/22 |
| 4,697,006 | 9/1987 | Ikenaka et al. | 536/17.3 |

FOREIGN PATENT DOCUMENTS

| | | | |
|---|---|---|---|
| 0031941 | 7/1981 | European Pat. Off. | |
| 0104047 | 3/1984 | European Pat. Off. | |
| 0135758 | 4/1985 | European Pat. Off. | |
| 3000292 | 7/1981 | Fed. Rep. of Germany | 435/22 |
| 58-71897 | 4/1983 | Japan | 435/22 |

OTHER PUBLICATIONS

Wilkinson, J. H., *The Principles and Practice of Diagnostic Enzymology*, (An Edward Arnold Publication) pp. 149–154, (1976).
Chemical Abstracts 82, 151408h (1975).
Chemical Abstracts 88, 148201d (1978).
Chemical Abstracts 90, 182383r (1979).
Chemical Abstracts 102, 221146d (1985).
Omichi et al, "The Journal of Biochemistry", vol. 97, No. 4, Apr. 1985, pp. 977–982.
Chemical Abstracts, vol. 101, No. 3, July 16, 1984, p. 289, Abstract 101: 19761z.

*Primary Examiner*—Ronald W. Griffin
*Attorney, Agent, or Firm*—Armstrong, Nikaido, Marmelstein & Kubovcik

[57] ABSTRACT

An oligosaccharide derivative having 4 to 7 glucose units wherein a primary alcohol moiety positioned at the 6-position of the non-reducing end glucose unit is replaced by

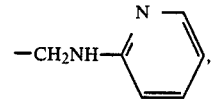

—CH$_2$OCH$_2$COOH, or the like group and the 1-position of the reducing end glucose unit is replaced by a phenoxy or substituted phenoxy group or an umbelliferyl group or an indoxyl group is particularly suitable as a substrate for measuring α-amylase activity.

12 Claims, 6 Drawing Sheets

OLIGOSACCHARIDE DERIVATIVES AND THEIR USE AS SUBSTRATE FOR MEASURING α-AMYLASE ACTIVITY

BACKGROUND OF THE INVENTION

This invention relates to an oligosaccharide derivative and a process for measuring α-amylase activity by using the oligosaccharide derivative as a substrate.

Measurement of α-amylase activity in a sample, particularly in saliva, pancreatic juice, blood and urine in human living body is important for diagnosis in medical science. For example, α-amylase activity in blood and urine shows a remarkable increase in the case of pancreatitis, cancer of the pancreas, and parotitis compared with normal values.

Various methods for measuring α-amylase activity have been reported. These methods can be divided into two groups, one of which is to use a long chain natural product such as starch, amylose, amylopectin, or the like or a modified material thereof as a substrate, and another of which is to use an oligosaccharide having 4 to 7 glucose units or a derivative thereof as a substrate.

Recently, methods of using uniform substances having definite structures as a substrate are to be employed widely in place of known methods using starch as a substrate. For example, there are proposed a method of using an oligosaccharide such as maltotetraose (G₄), maltopentaose (G₅), maltohexaose (G₆), or maltoheptaose (G₇) as a substrate (Chem. Abstr. 82, 151408 h (1975); ibid. 88, 148201 d (1978)), a method of using an oligosaccharide bonding a chromogen such as p-nitrophenol at a reducing end thereof (Chem. Abstr., 90, 182383 r (1979)), etc.

These methods generally require such a coupling enzyme for the measurement as α-glucosidase (E.C. 3.2.1.20: α-D-glucoside glucohydrolase), glucoamylase (E.C. 3.2.1.3: 1,4-α-D-glucan glucohydrolase), or β-glucosidase (E.C. 3.2.1.21: β-D-glucoside glucohydrolase). Since these coupling enzymes are exo type enzymes which hydrolyze an α-1,4-glucoside bond from a non-reducing end of saccharide chain having α-1,4-glucoside bonds, they have a defect in that they decompose the substrates irrespective of the α-amylase reaction. Therefore, in the above-mentioned measuring methods using these coupling enzymes, a reagent solution for the measurement becomes unstable, and reagent blank values become remarkably high, which results in making measuring accuracy remarkably worse. Further, since a sufficient amount of glucoamylase or α-glucosidase necessary for the measurement cannot be used, it is difficult to construct a measuring method with high accuracy.

In order to solve such problems, the present inventors have synthesized modified oligosaccharides represented by the formula:

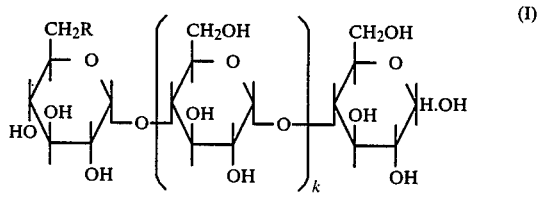

(I)

wherein the rightmost glucose unit is a reducing group; k is an integer of 2 to 5; and R is an organic residue such as a pyridylamino group, and used them as a substrate for measuring α-amylase activity (European Patent Publication No. 0104047 A2). These substances are uniform and definite in structure as the substrate and characterized by not becoming a substrate for α-glucosidase, β-glucosidase or glucoamylase. When these substances are used as a substrate for measuring α-amylase activity, there must employ either a high performance liquid chromatographic method or a method wherein a coupling enzyme such as α-glucosidase, β-glucosidase or glucoamylase is used to produce glucose which is subjected to the measurement. Therefore, this method has problems in that a special device should be used in the former case and an influence of glucose contained in a sample cannot be neglected in the latter case, and the like.

On the other hand, Chem. Abstr., 102, 221146d (1985) discloses an oligoglucoside derivative of the formula:

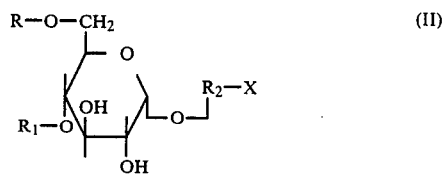

(II)

wherein R and R₁ are independently a straight-chain or branched alkyl or alkoxy group having 1 to 6 carbon atoms or a phenyl group, R and R₁ in combination being able to form a methylene bridge and at least one of hydrogen atoms may independently be substituted with an alkyl group having 1 to 5 carbon atoms or a phenyl group; R₂ is a glucoside group having 2 to 7 glucose units; and X is hydrogen or a group which can be measured optically, particularly a nitrophenyl group, and a method for measuring α-amylase activity by using such an oligoglucoside derivative as a substrate. But when R and R₁ are alkyl, alkoxy or phenyl groups, it is difficult to synthesize the compound of the formula (II) in good yield (due to the introduction of these groups into the hydroxyl groups at the 2- and 3-positions, difficulty in isolation and poor yield). On the other hand, when R and R₁ together form a methylene bridge, the resulting ethylidene type compound of the formula (II) is unstable (even at neutral) when used as a substrate. Further, the compound of the formula (II) has some problems in that the efficiency of this compound as a substrate is poor.

As mentioned above, substrates heretofore known are not satisfactory and require further improvement.

SUMMARY OF THE INVENTION

It is an object of this invention to provide an oligosaccharide derivative which can overcome the problems mentioned above when used as a substrate for measuring α-amylase activity. It is a further object of this invention to provide a process for measuring α-amylase activity using such an oligosaccharide derivative as a substrate.

This invention provides an oligosaccharide derivative represented by the formula:

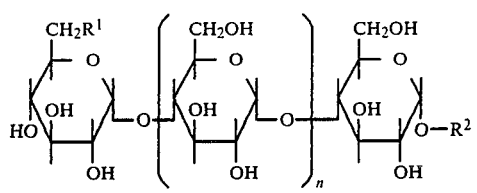

(III)

wherein n is an integer of 2 to 5; $R^1$ is a pyridylamino group, an anilino group, a substituted anilino group, a lower alkylamino group, a carboxymethoxy group or a salt thereof; and $R^2$ is a group of the formula:

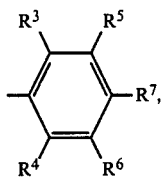

(IV)

in which $R^3$ through $R^6$ are independently hydrogen, a lower alkyl group, a lower alkoxy group, a nitro group, a carboxyl group, a sulfone group or a halogen; and $R^7$ is hydrogen, a lower alkoxy group, a halogen or a nitro group, or a group of the formula:

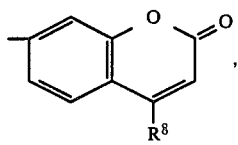

(V)

in which $R^8$ is hydrogen or a methyl group, or a group of the formula:

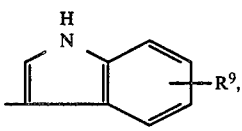

(VI)

in which $R^9$ is hydrogen or a halogen.

This invention also provides a process for measuring α-amylase activity using the oligosaccharide derivative of the formula (III) as a substrate.

DESCRIPTION OF THE PREFERRED EMBODIMENTS

Figure 1:
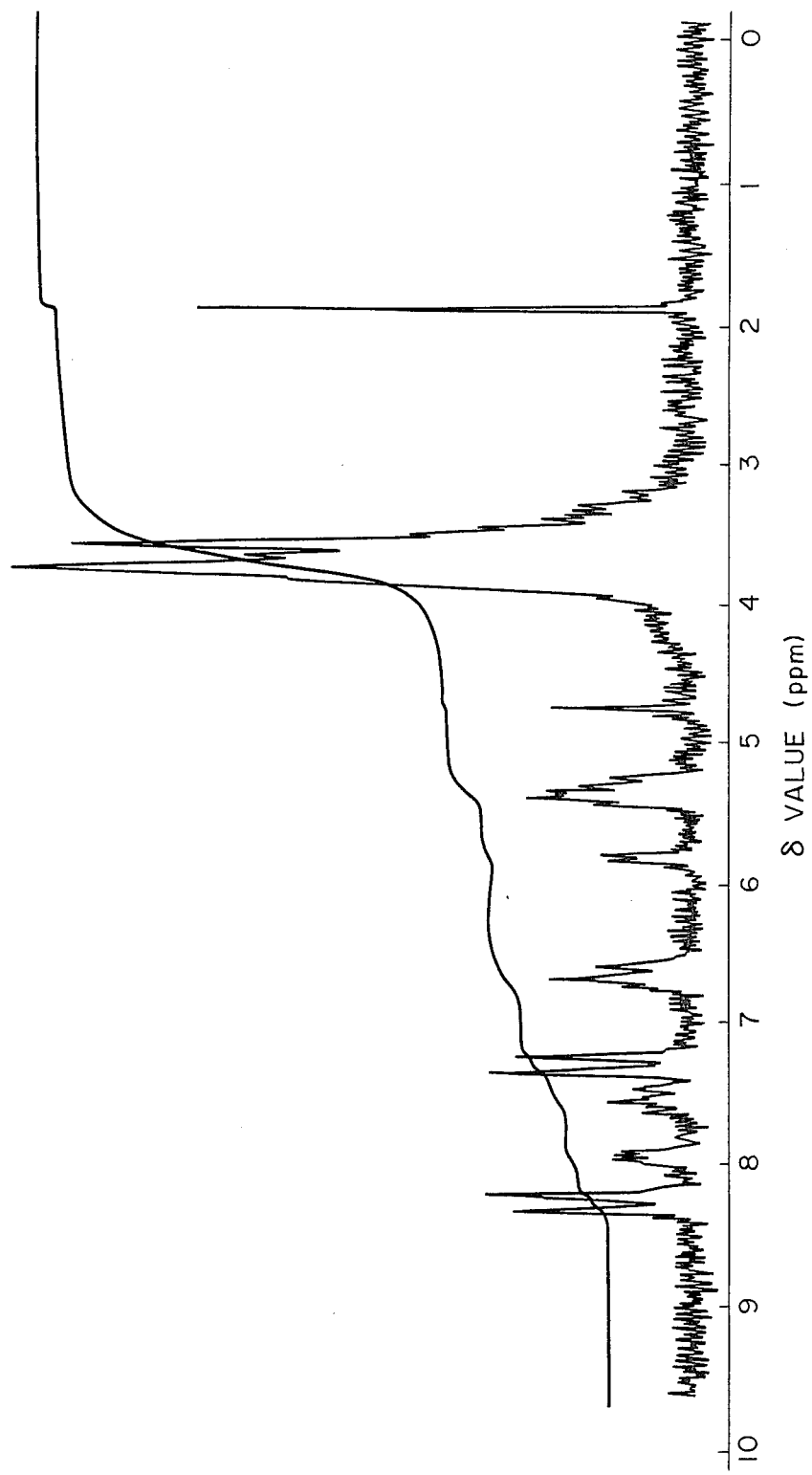
FIG. 1 is a $^1$H-NMR spectrum of FG5PNP produced in Example 1 in $D_2O$.

The oligosaccharide derivative of this invention is represented by the formula:

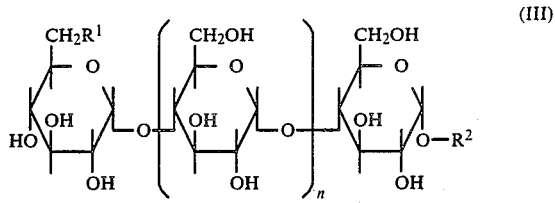

(III)

wherein n is an integer of 2 to 5; $R^1$ is a pyridylamino group such as a 2-pyridylamino group or a 3-pyridylamino group, an anilino group or a substituted anilino group such as a methylanilino group, a hydroxyanilino group, a carboxyphenylamino group, or the like, a lower alkylamino group preferably having 1 to 4 carbon atoms such as a methylamino group, an ethylamino group, a propylamino group, or the like, a carboxymethoxy (—OCH$_2$COOH) group or a salt (an alkali metal (e.g. Na, K, Li, etc) salt or an ammonium salt) thereof; and $R^2$ is a group of the formula:

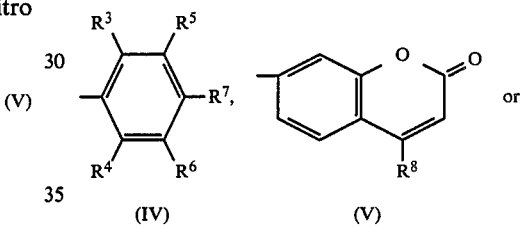

(IV)         (V)

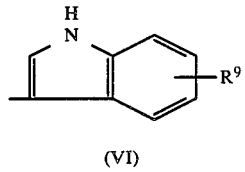

(VI)

wherein $R^3$ through $R^6$ are independently hydrogen, a lower alkyl group preferably having 1 to 4 carbon atoms, a lower alkoxy group preferably having 1 to 4 carbon atoms, a nitro group, a carboxyl group, a sulfone group or a halogen such as F, Cl, Br, or I; $R^7$ is hydrogen, a lower alkoxy group preferably having 1 to 4 carbon atoms, a halogen such as F, Cl, Br or I, or a nitro group; $R^8$ is hydrogen or a methyl group; and $R^9$ is hydrogen or a halogen such as F, Cl, Br, or I.

The substituent of the formula (IV) and —O— form a substituted phenoxy group which is bonded to the reducing end of the oligosaccharide and is able to be hydrolyzed by the action of glucoamylase, α-glucosidase or β-glucosidase. After the hydrolysis, the resulting product should have an absorption in a visible light range such as nitrophenols, or can produce a dye by coupling with a coupler by an action of an oxidase such as catechol oxidase, laccase, tyrosinase or monophenol oxidase, or can produce a dye by coupling with a coupler by an oxidant. Examples of the group of the formula (IV) are a p-nitrophenyl group, a m-nitrophenyl group, an o-chlorophenyl group, a p-chlorophenyl group, a 2,6-dichlorophenyl group, an o-methoxyphenyl group, a p-methoxyphenyl group, an o-methylphenyl group, an o-carboxyphenyl group, an o-sulfophenyl group, etc.

The group of the formula (V) forms together with —O— an umbelliferyl group or 4-methylumbelliferyl group.

The group of the formula (VI) forms together with —O— an indoxyl group.

Among oligosaccharide derivatives of the formula (III), the following compounds are preferable:

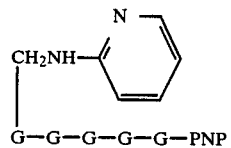
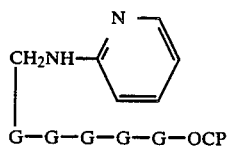
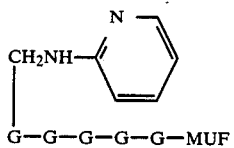
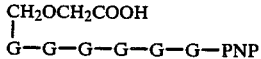
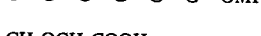
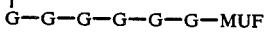
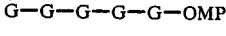
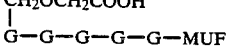

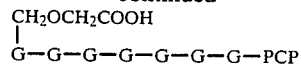
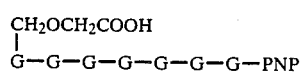
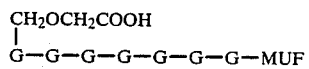
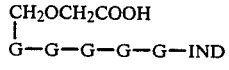
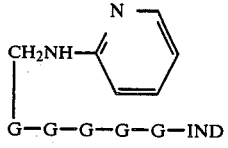
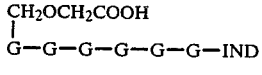
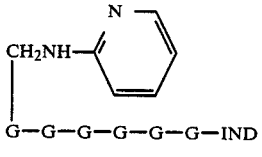

In the above formulae, G is a glucose unit, PNP is a p-nitrophenoxy group, OCP is an o-chlorophenoxy group, MUF is a 4-methylumbelliferyl group, PCP is a p-chlorophenoxy group, OMP is an o-methoxyphenoxy group, and IND is an indoxyl group.

The oligosaccharide derivative of the formula (III) can be synthesized by using as a starting material a polysaccharide such as dextrin, amylose, or the like as follows.

SYNTHESIS EXAMPLE 1

(1) An oligosaccharide derivative wherein the primary alcohol residue at the 6-position of non-reducing end glucose is replaced by a 2-pyridylamino group is synthesized according to the process disclosed in J. Biochemistory, vol. 93, p. 1055 (1983).

That is, the primary alcohol at the 6-position of glucose residue of dextrin is partially oxidized with dimethyl sulfoxide and N,N'-dicyclohexylcarbodiimide, reacted with 2-aminopyridine to form a Schiff's base, followed by reduction with cyanoborohydride to yield dextrin introducing a 2-aminopyridyl group thereinto. The resulting product is reacted with a liquefied type α-amylase derived from the bacillus genus and glucoamylase to give a mixed oligosaccharide derivatives introducing a 2-pyridylamino group into the non-reducing end glucose. After denaturing the added α-amylase and glucoamylase with heating at 100° C. for 10 minutes, insoluble materials are removed by filtration. The filtrate is purified by ion exchange column chromatography to give a fraction of O-b-deoxy-6-[(2-pyridyl)amino]-α-D-glucopyranosyl-(1→4)-O-α-D-glucopyranosyl-(1→4)-O-α-D-glucopyranosyl-(1→4)-O-α-D-glucopyranosyl-(1→4)-O-α-D-glucopyranosyl-(1→4)-D-glucopyranose (FG 6) of the formula:

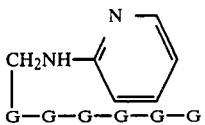

wherein G is a glucose unit.

(2) To the resulting product, p-nitrophenyl-α-D-glucoside, o-chlorophenyl-α-D-glucoside, or 4-methyl-umbelliferyl-α-D-glucoside or indoxyl-α-D-glucoside, and cyclomaltodextrin-glucanotransferase (E.C. 2.4.1.19) derived from the bacillus genus are added and reacted. This reaction can be shown as follows:

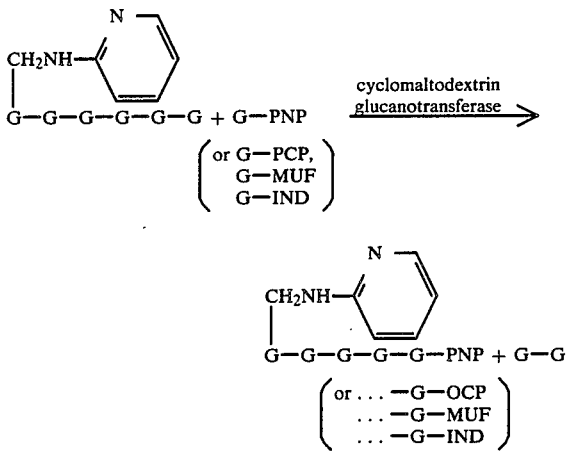

wherein G is a glucose unit; PNP is a p-nitrophenoxy group; OCP is an o-chlorophenoxy group; MUF is a 4-methylumbelliferyl group, and IND is an indoxy group. Purification of the reaction solution by gel filtration gives the desired product:

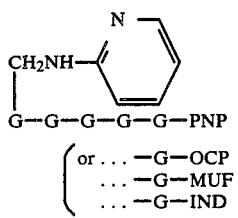

i.e., O-6-deoxy-6-[(2-pyridyl)amino]-α-D-glucopyranosyl-( 1→4)-O-α-D-glucopyranosyl-(1→4)-O-α-D-glucopyranosyl-(1→4)-O-α-D-glucopyranosyl-(1→4)-p-nitrophenylglucopyranose (FG5PNP) (or . . . -o-chlorophenylglucopyranose (FG5OCP), or . . . -4-methylumbelliferylglucopyranose (FG5MUF), or . . . -indoxylglucopyranose (FG5IND)).

SYNTHESIS EXAMPLE 2

(1) An oligosaccharide derivative wherein the primary alcohol residue at the 6-position of non-reducing end glucose is replaced by a carboxymethyl group is synthesized according to the process disclosed in Japanese Patent Unexamined Publication No. 31699/84.

That is, amylose having a molecular weight of about 15,000 to 200,000, sodium hydroxide and monochloroacetic acid are reacted in an aqueous solution. The alkali is used in an amount of 5 to 30 moles and the monochloroacetic acid is used in an amount of about 0.5 to 2.5 moles per mole of the glucose unit of amylose. The reaction proceeds by heating at 30° to 70° C. for 30 minutes to 3 hours with stirring. By this reaction, a modified amylose having a carboxymethyl group or a salt thereof per about 15 to 30 glucose units can be obtained.

Then, the product is neutralized and subjected to dialysis using water as an outer solution to remove reaction by-products such as sodium chloride, sodium hydroxyacetate, etc. This solution is added to a buffer solution of about pH 5 to 7 and α-amylase is added thereto, followed by a reaction at 37° C. for a predetermined time.

After the reaction, the reaction solution is heated at a temperature of 70° C. or higher for 30 to 60 minutes to deactivate the α-amylase. After the heat treatment, the reaction solution is cooled to about 20° C. and the pH of the reaction solution is adjusted to neutral of pH 6 to 8. Then, α-glucosidase or glucoamylase is added thereto, followed by incubation at 37° C. for 10 to 30 hours to decompose the α-1,4-glucoside linkage from the non-reducing end of oligosaccharide derivative produced by the action of α-amylase. As a result, an oligosaccharide derivative having a carboxymethyl group or a salt thereof at the non-reducing end glucose unit is obtained.

Then, the resulting mixture is condensed, followed by chromatography by gel filtration according to the process of H. Kondo et al [Agric. Biol. Chem., 45, 2369 (1981)] to give the desired oligosaccharide derivatives, that is, indivudual fractions of maltopentaose, maltohexaose and maltoheptaose, each having a carboxymethyl group or a salt thereof at the non-reducing end.

(2) After condensing each fraction obtained above, p-nitrophenyl-α-glucoside or o-methoxyphenyl-α-glucoside or 4-methylumbelliferyl-α-glucoside or indoxyl-α-glucoside and cyclomaltodextrin glucanotransferase (E.C. 2.4.1.19) are added to each fraction and reacted. This reaction can be shown as follows:

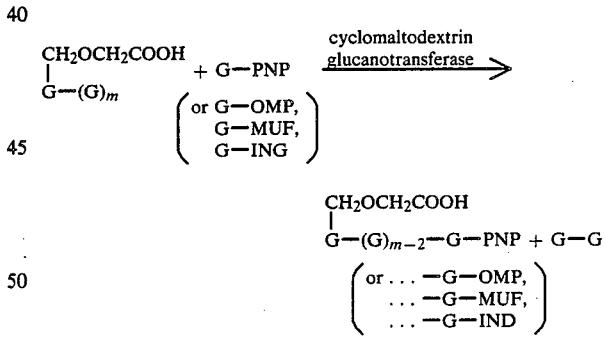

wherein G is a glucose unit; PNP is a p-nitrophenoxy group; OMP is an o-methoxyphenoxy group; MUF is a 4-methylumbelliferyl group; IND is an indoxyl group; and m is an integer of 4 to 6.

The reaction solution is purified by gel filtration to give the desired oligosaccharide derivatives, that is, maltotetraose, maltopentaose and maltohexanose, each having a carboxymethyl group or a salt thereof at the non-reducing end and a p-nitrophenoxy group, or an o-methoxyphenoxy group, or a 4-methylumbelliferyl group or an indoxyl group at the reducing end.

SYNTHESIS EXAMPLE 3

Each fraction of maltotetraose, maltopentaose, maltohexanose and maltheptaose, each having carboxymethyl group or a salt thereof at the non-reducing end, is obtained in the same manner as described in Synthesis Example 2. After condensing each fraction, α-D-glucopyranosyl-(1→4)-D-[1-(p-nitrophenoxy)-glucopyranose], or α-D-glucopyranosyl-(1→4)-D-[1-(p-chlorophenoxy)glucopyranose], or α-D-glucopyranosyl-(1→4)-D-[1-(4-methylumbelliferyl)-glucopyranose], or α-D-glucopyranosyl-(1→4)-D-[1-(indoxyl)-glucopyranose] and cyclomaltodextrin glucanotransferase derived from Bacillus species are added to each fraction and reacted. This reaction can be shown as follows:

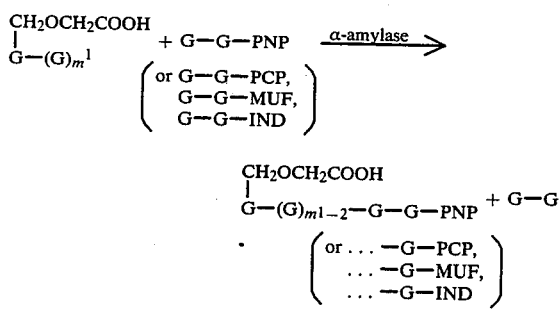

wherein G is a glucose unit; PNP is a p-nitrophenoxy group; PCP is a p-chlorophenoxy group; MUF is a 4-methylumbelliferyl group; and $m^1$ is an integer of 3 to 6. The reaction solution is purified by gel filtration to give the desired oligosaccharide derivatives, that is, maltotetraose, maltopentaose, maltohexaose and maltoheptaose, each having a carboxymethyl group or a salt thereof at the non-reducing end and a p-nitrophenoxy group, or a p-chlorophenoxy group, or a 4-methylumbelliferyl group or an indoxyl group at the reducing end.

The oligosaccharide derivative of the formula (III) can be used as a substrate for measuring α-amylase activity in the following manner in principle:

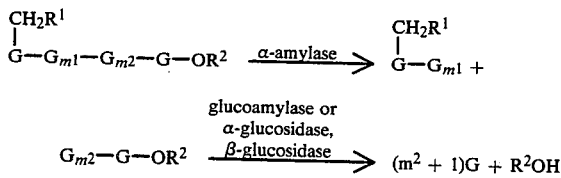

In the above formulae, G is a glucose unit; $R^1$ and $R^2$ are as defined in the formula (III), $m^1$ and $m^2$ are integers of 1 or more and $m^1+m^2=2$ to 5.

That is, α-amylase in a sample acts on the oligosaccharide of the formula (III) to yield

including the non-reducing end having the substituent $CH_2R^1$ at the 6-position, and $G_{m2}$—G—OR$^2$ having the substituted phenoxy group or umbelliferyl group or indoxyl group at the reducing end. Then, $G_m$—G—OR$^2$ is reacted with a coupling enzyme such as glucoamylase, α-glucosidase or β-glucosidase to form $(m^2+1)G$ and $R^2OH$.

When $R^2$—OH is a nitrophenol such as p-nitrophenol, the α-amylase activity in the sample can be obtained by directly measuring absorption spectrum (e.g., absorbance at 405 nm). When $R^2$—OH is a phenol having no nitro group such as phenol, o-chlorophenol, 2,6-dichlorophenol, p-methoxyphenol or the like (this can also be applied to the case having a nitro group), $R^2$—OH is reacted with an oxidase such as catechol oxidase, laccase, tyrosinase or monophenol oxidase, or an oxidizing agent such as iodic acid or periodic acid and subjected to coupling (oxidative condensation) with a coupler such as 4-aminoantipyrine, 3-methylbenzothiazolynonehydrazone (MBTH), or the like so as to yield a dye, an absorption spectrum of which is measured to obtain the α-amylase activity in the sample. When $R^2$—OH is a compound having fluorescence such as umbelliferone or 4-methylumbelliferone, the α-amylase activity in the sample can be obtained by measuring its fluorescence intensity.

When $R^2$—OH is an indole compound such as indole, 5-chloroindole, 5-bromoindole or the like, $R^2$—OH is oxidized by air to carry out self-coupling so as to yield an indigo dye, an absorption spectrum of which is measured (e.g. absorbance at 600 nm, etc.) to obtain the α-amylase activity in the sample.

In the measurement of α-amylase activity, the concentration of the oligosaccharide derivative of the formula (III) used as a substrate is not particularly limited, but preferably is about 0.1 to 10 mM.

Any samples containing α-amylase can be measured by the process of this invention. Examples of such samples are blood, serum, urine and the like derived from a living body.

The coupling enzyme, that is, glucoamylase, α-glucosidase or β-glucosidase, is not particularly limited and that derived from an aminal, a plant or a microorganism can be used alone or as a mixture thereof. The using amount of the coupling agent is usually 5 to 50 units/ml, preferably 10 to 30 units/ml.

The reaction temperature necessary for the measurement is not particularly limited, but preferably at about 25° to 40° C. The reaction time can be selected optionally.

The reaction is carried out preferably at a pH of about 6 to 8. In order to maintain the preferable pH, there can be used a buffering agent such as a phosphate buffer, trishydroxymethylaminomethane-HCl buffer, Good's buffer, etc.

As an activating agent for α-amylase, there can be used sodium chloride, calcium chloride, potassium chloride, etc.

As the coupler for coupling (oxidative condensation) the phenols freed by the action of coupling enzyme, there can be used 4-aminoantipyrine, 3-methylbenzothiazolinonehydrazone (MBTH), p-amino-N,N-diethylaniline, etc.

As the oxidase for coupling (oxidative condensation) the phenols with the coupler, there can be used laccase, catechol oxidase, tyrosinase, monophenol oxidase, etc., derived from animals, plants and microorganisms in an amount of usually 0.2 to 10 units/ml, preferably 0.5 to 4 units/ml.

As the oxidant for the coupling (oxidative condensation), there can be used iodic acid and/or an alkali metal salt thereof, periodic acid and/or an alkali metal salt thereof, hydrogen peroxide, etc.

The α-amylase activity can be measured either by a kinetic assay wherein the reaction rate is measured under constant conditions, or an end point assay wherein a reaction terminator is used.

When the oligosaccharide of the formula (III) is used as a substrate, it is also possible to employ a so-called colorimetry wherein the degree of coloring of a dye is measured. Therefore, a test-paper method which is very simple and a so-called dry quantitative method wherein multi-layer analysis sheets impregnated with reaction reagents (a multi-layered quantitative analysis film) can also be used.

Since the oligosaccharide derivative of the formula (III) has a substituted group ($-CH_2R^1$ in which $R^1$ is as defined above) at the 6-position of non-reducing end glucose unit in place of a primary alcohol moiety ($-CH_2OH$), it cannot become a substrate for glucoamylase, $\alpha$-glucosidase or $\beta$-glucosidase as it is, it is soluble in water and it is excellent in affinity for $\alpha$-amylase. Therefore, it can be a good specific substrate for $\alpha$-amylase. Since the oligosaccharide derivative of the formula (III) has excellent properties as mentioned above, the measuring process according to this invention has advantages in that no side reaction takes place, reagent blank values are remarkably small, and reagent solutions for the measurement are remarkably stable. Further, since a single compound is used as a substrate, stoichiometry of the reaction is established and kinetic detection of $\alpha$-amylase becomes possible.

Further, since the coupling enzyme such as glucoamylase, $\alpha$-glucosidase or $\beta$-glucosidase can be used in a sufficient amount, the reaction rate after the $\alpha$-amylase reaction is fast and more correct and more precise measurement of $\alpha$-amylase activity becomes possible.

In addition, in the $\alpha$-amylase activity measurement according to this invention, since the detection is carried out by measuring absorption spectra of nitrophenols freed, or indigo dyes or measuring absorption spectra of dyes obtained by oxidative coupling of phenols freed with 4-aminoantipyrine, MBTH, or the like, or measuring fluorescence intensity of umbelliferones freed, influences of saccharides such as glucose, maltose, etc., and reducing substances such as ascorbic acid, bilirubin, etc., present in the sample are hardly shown. Further, the measuring process of this invention can be well applied to an outoanalyzer as well as a manual method if required.

This invention is illustrated by way of the following Examples.

EXAMPLE 1

Synthesis of an oligosaccharide derivative FG5PNP represented by the formula:

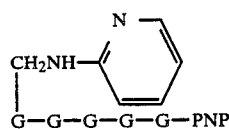

(VII-b)

(1) Synthesis of FG6 of the formula:

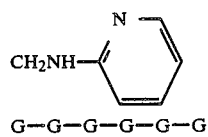

(VII-a)

In 38 ml of dimethyl sulfoxide, 2 g of amylose and 3 g of N,N'-dicyclohexylcarbodiimide were dissolved, and a mixture of 0.4 ml of dichloroacetic acid and 4 ml of dimethyl sulfoxide was added thereto, followed by reaction at 20° to 25° C. for 50 minutes. To this, a solution obtained by dissolving 1.2 g of oxalic acid (dihydrate) in 5 ml of methanol was added to stop the reaction. To the resulting reaction mixture, a 2-aminopyridine solution (a mixed solution of 8.5 g of 2-aminopyridine, 12 ml of water, 3 ml of acetic acid and 3.2 g of sodium cyanoborohydride) was added and heated at 90° C. for 30 minutes. After the hydrogenation reaction, 300 ml of water was added to the reaction mixture and a precipitate produced was filtered. The filtrate was made pH 1.0 with 6N HCl. After decomposing excess sodium cyanoborohydride, the reaction mixture was made pH 7.0 with 1N NaOH, and concentrated under reduced pressure. The concentrate was dissolved in water and subjected to gel filtration. A column having a diameter of 4.5 cm and a height of 90 cm packed with Biogel P-4 (available from Bio Rad Lab.) which is equilibrated with 10mM ammonium bicarbonate was used to collect high polymer fractions, followed by freeze-drying.

The yield was about 1.6 g and the modification in terms of glucose unit from absorbance at 310 nm in 0.1M acetic acid was 7.4%.

This modified amylose in an amount of 1.5 g was dissolved in 160 ml of water and the pH of the resulting solution was made 4.8 with 1N HCl. To this, 10 mg of glucoamylase derived from Rhizopus niveus was added and incubated at 40° C. for 5 hours. After the reaction, the reaction mixture was made pH 6.0 with 1N NaOH. Then, 16 ml of a buffer solution (pH 6.0) of 0.1M calcium acetate containing 0.013% liquefying type $\alpha$-amylase derived from Bacillus subtilis was added to the reaction mixture and incubated at 40° C. for 1 hour. Subsequently, the resulting reaction mixture was heated at 100° C. for 10 minutes to deactivating the enzyme and the pH was made 4.8 with 1N HCl. To this liquid, 5 mg of glucoamylase derived from Rhizopus niveus was added and incubated at 40° C. for 5 hours. Then, the total amount was made 750 ml by adding water thereto. Then, 250 ml out of the 750 ml solution was subjected to column chromatography using a column packed with Dowex 50 W×2 (mfd. by Dow Chemical Co.) equilibrated with 0.1M pyridine-acetate buffer (pH 5.6). The column had a diameter of 1.5 cm and a height of 124 cm. The eluation was conducted by linear concentration gradient of 0.1M pyridine-acetate buffer (pH 5.6) and 0.35M pyridine-acetate buffer pH 5.6). The detection was conducted by UV absorption at 310 nm.

The fraction of FG6 was concentrated under reduced pressure to give the desired product in an amount of 60 mg.

(2) Synthesis of FG5PNP represented by the formula:

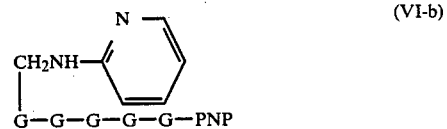

(VI-b)

FG6 obtained in above (1) in an amount of 54 mg and 130 mg of p-nitrophenyl-$\alpha$-glucoside were dissolved in 30 ml of 0.1M calcium acetate buffer (pH 6.0) and 10 ml of a solution of 0.6 U/ml of cyclomaltodextrin-glucanotransferase derived from Bacillus macerans was added thereto. The incubation was conducted at 37° C. for 10 minutes, followed by addition of 4 ml of acetic acid. Then, the resulting reaction solution was subjected to gel filtration using a column having a diameter of 2.5 cm and a height of 266 cm packed with Bio gel P-2 (available from Bio Rad Lab.) which is equlibrated with 40mM acetic acid. The detection was conducted by absorption at 310 nm.

After concentrating the fraction of FG5PNP under reduced pressure, the desired product was obtained in 14 mg (yield 25%). The purification was conducted by high performance liquid chromatography using a column (10×250 mm) packed with Cosmosil 5C$_{18}$ (available from Nakarai Chemical, Ltd., C$_{18}$ reverse phase), 0.1M acetic acid containing 0.8% 1-butanol as an eluate with a flow rate of 3.5 ml/min.

(3) Identification of Structure

The structure of FG5PNP was identified as follows.

To 100 μl of 2mM FG5PNP, 30 μl of 1 U/ml α-amylase derived from human saliva (available from Sigma Chemical Co.) was added and incubated at 37° C. for 1 hour. Then, the reaction products were analyzed by using thin layer chromatography and high performance liquid chromatography. That is, as the thin layer chromatography, DC-Alufolien Kies elgel 60 (available from Merck & Co., Inc.) was used and a mixture of methyl ethyl ketone, acetic acid and water (3:1:1 by volume) was used as a developing solvent. As samples, FG5PNP, the above-mentioned reaction products and p-nitrophenyl-α-maltoside were developed. As to the reaction products, two other spots were obtained in places different from that of FG5PNP, the one being in agreement with the spot place of p-nitrophenyl-α-maltoside and the other being a spot having fluorescence.

In the case of high performance liquid chromatography, a column (4.6×150 mm) packed with Cosmosil 5C$_{18}$ (Nakarai Chemical, Ltd., C$_{18}$ reverse phase) was used. A buffer of 0.1M ammonium acetate (pH 3.6) containing 0.05% 1-butanol was flowed at a rate of 1.8 ml/min and the detection was conducted by using fluorescence with excitation wavelength of 320 nm and fluorescence wavelength of 400 nm.

When a sample of O-6-deoxy-6-[(2-pyridyl)amino]-α-D-glucopyranosyl-(1→4)-O-α-D-glucopyranosyl-(1→4)-O-α-D-glucopyranose was measured under the same conditions of high performance liquid chromatography as mentioned above, the same retention time as the above-mentioned reaction products was obtained. Further, since FG5PNP was not hydrolyzed by glucoamylase, the introduction of a modifying group into the non-reducing end was also identified. FIG. 1 shows $^1$H-NMR spectrum of FG5PNP in D$_2$O.

EXAMPLE 2

Synthesis of oligosaccharide derivative of the formula:

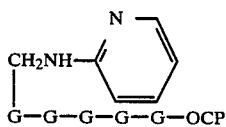

FG6 obtained in the same manner as described in Example 1 (1) in an amount of 54 mg and 130 mg of o-chloro-phenyl-α-glucoside were dissolved in 30 ml of 0.1M calcium acetate buffer (pH 6.0) and 10 ml of a solution of 0.6 U/ml cyclomaltodextrin-glucanotransferase was added thereto to incubate at 37° C. for 10 minutes. After the reaction, 4 ml of acetic acid was added thereto. The resulting reaction mixture was subjected to gel filtration using a column having a diameter of 2 cm and a height of 260 cm packed with Biogel P-2 (available from Bio Rad Lab.) which is equilibrated with 40mM acetic acid. The detection was conducted by absorption at 270 nm.

The fraction of O-6-deoxy-6-[(2-pyridyl)amino]-α-D-glucopyranosyl-(1→4)-O-α-D-glucopyranosyl-(1→4)-O-α-D-glucopyranosyl-(1→4)-O-′-D-glucopyranosyl-(1→4)-D-[1-(o-chlorophenoxy)-glucopyranose] (FG5OGP) represented by the formula:

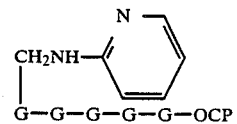

was concentrated under reduced pressure to yield 20 mg of the desired product. The purification was conducted by high performance liquid chromatography using a column (10×250 mm) packed with Cosmosil 5C$_{18}$ (Nakarai Chemical, Ltd., C$_{18}$ reverse phase) and 0.1M acetic acid containing 0.8% 1-butanol as an eluate with a flow rate of 3.5 ml/min.

The identification of the desired product was conducted in the same manner as described in Example 1 (3) to identify that the desired product was obtained.

EXAMPLE 3

[Measuring Reagents]

(1) Reagent Solution 1

An aqueous solution containing 100mM of 3,3-dimethylglutaric acid and 40mM of sodium chloride was prepared and made pH 6.8 with NaOH. To this solution, α-glucosidase was added and dissolved so as to make the concentration 185 U/ml.

(2) Reagent Solution 2

An aqueous solution of 3.1mM FG5PNP produced in Example 1 was prepared.

[Measuring Procedures]

To 3 ml of Reagent Solution 1, 1 ml of sample serum was added, and then 1 ml of Reagent Solution 2 was added thereto, followed by incubation at 37° C. for 15 minutes. To 0.5 ml of the reaction solution, 2 ml of 2% sodium carbonate solution was added and absorbance at a wavelength of 405 nm was measured.

Figure 2:
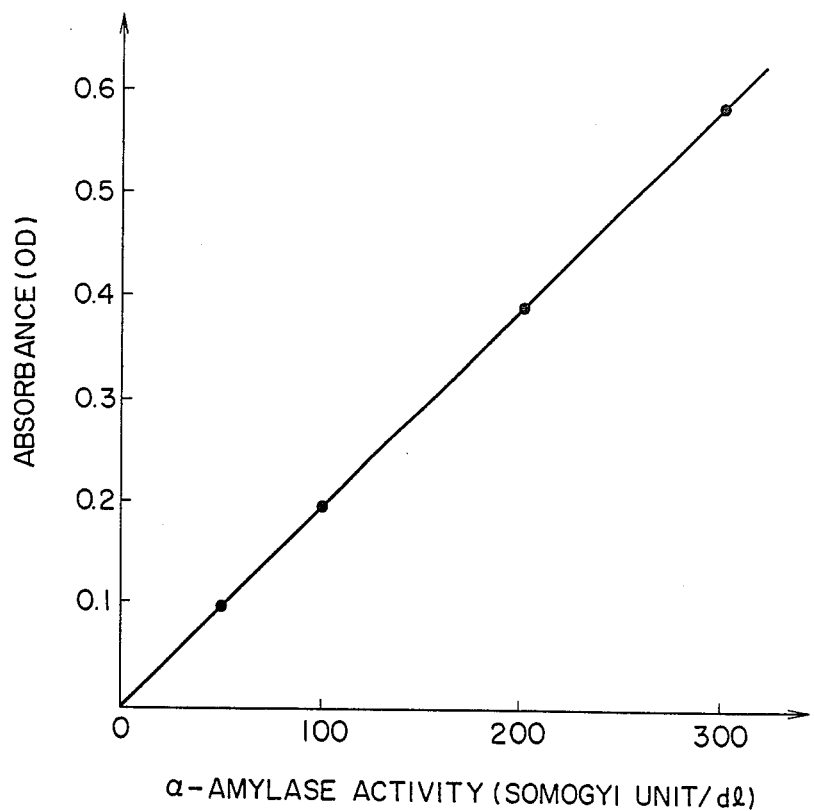
FIG. 2 is a graph showing a calibration curve obtained in Example 3, wherein α-amylase activity (Somogyi unit/dl) is taken along the abscissa axis and absorbance (OD) is taken along the ordinate axis.

On the other hand, using standard samples of known α-amylase activity, a calibration curve was obtained by the same procedure as mentioned above. From this calibration curve, the α-amylase activity in the sample was obtained. FIG. 2 shows a relationship between the α-amylase activity (Somogyi units/dl) at individual dilution stages of standard samples and the absorbance (OD) at a wavelength of 405 nm.

EXAMPLE 4

[Measuring Reagent]

(1) Reagent Solution 1

An aqueous solution was prepared by dissolving 15 mg of O-6-carboxymethyl-α-D-glucopyranosyl-(1→4)-O-α-D-glucopyranosyl-(1→4)-O-α-D-glucopyranosyl-(1→4)-O-α-D-glucopyranosyl-(1→4)-O-α-D-glucopyranosyl-(1→4)-D-[1-(p-nitrophenoxy)-glucopyranose] (CMG6PNP) obtained according to Synthesis Example 2, 20 mmole of HEPES (N-2-hydroxyethylpiperidine-N′-2-ethanesulfonic acid), 10 mmole of calcium chloride and 500 units of glucoamylase in purified water and made pH 6.9 with NaOH and a total amount of 20 ml with purified water.

[Measuring Procedures]

To 2 lml of Reagent Solution 1, 100 μl of sample serum was added and incubated at 37° C. Changes of absorbances of the reaction solution at a wavelength of 405 nm were measured.

Figure 3:
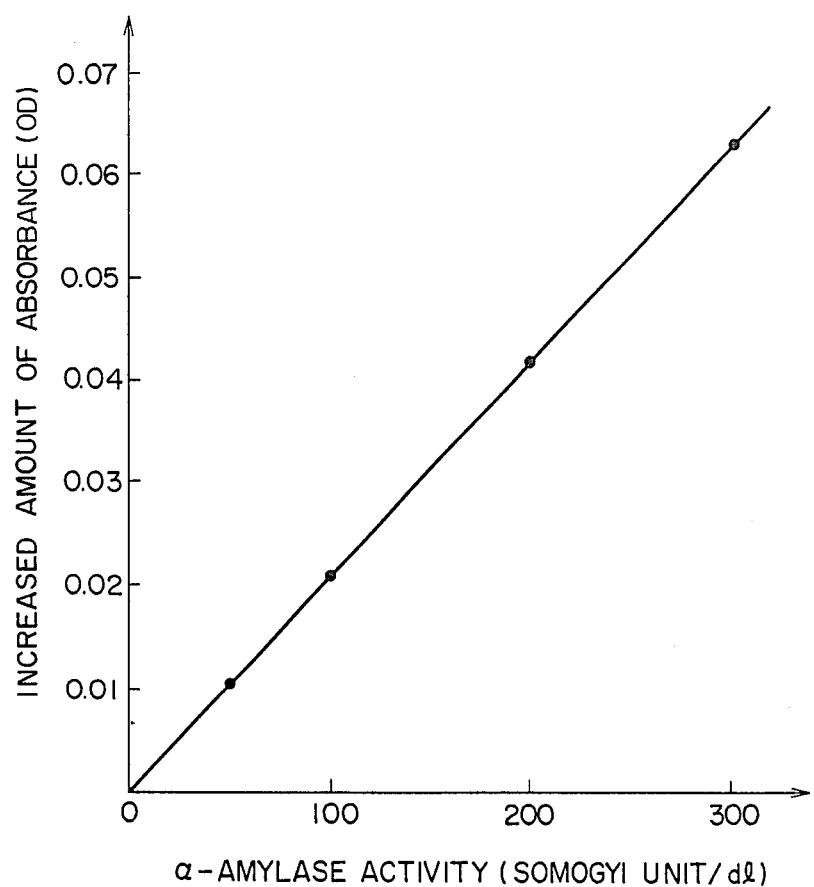
FIGS. 3, 4 and 5 are graphs showing calibration curves obtained in Examples 4, 5 and 6, respectively, wherein α-amylase activity (Somogyi unit/dl) is taken along the abscissa axis and an increase amount of absorbance (OD) is taken along the ordinate axis.

On the other hand, using standard samples of known α-amylase activity, a calibration curve was obtained by the same procedure as mentioned above. From this calibration curve, the α-amylase activity in the sample was obtained. FIG. 3 shows a relationship between the α-amylase activity (Somogyi units/dl) at individual dilution stages of standard samples and the increased amount of absorbance (OD) per minute at a wavelength of 405 nm.

EXAMPLE 5

[Measuring Reagent]

(1) Reagent Solution 1

An aqueous solution was prepared by dissolving 10 mmole of sodium acetate, 10 mmole of calcium acetate, 20 mg of FG5OCP synthesized in Example 2, 3 mg of 4-aminoantipyrine, 500 units of glucoamylase and 40 units of laccase in purified water, and made pH 6.9 with NaOH and a total amount 20 ml with purified water.

[Measuring Procedures]

To 2 ml of Reagent Solution 1, 100 μl of sample serum was added and incubated at 37° C. Increased amount of absorbance of the reaction solution per minute was measured at a wavelength of 505 nm.

Figure 4:
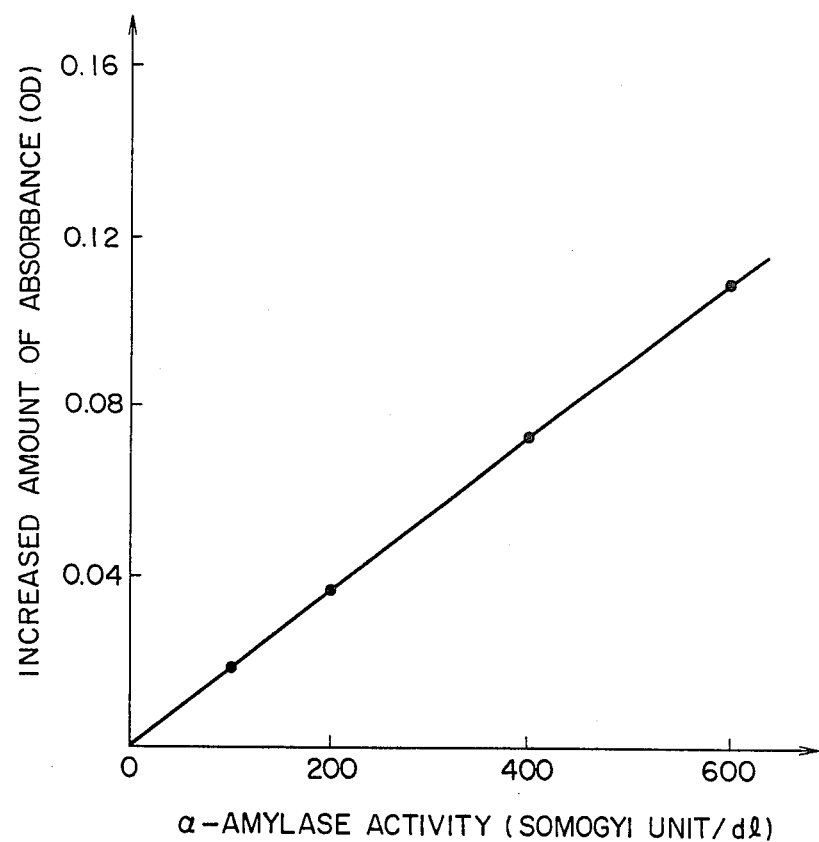

On the other hand, using standard samples of known α-amylase activity, a calibration curve was obtained by the same procedure as mentioned above. From this calibration curve, the α-amylase activity in the sample was obtained. FIG. 4 shows a relationship between the α-amylase activity (Somogyi units/dl) at individual dilution stages of standard samples and the increased amount of absorbance (OD) per minute at a wavelength of 505 nm.

EXAMPLE 6

[Measuring Reagent]

(1) Reagent Solution 1

An aqueous solution was prepared by dissolving 15 mg of O-6-carboxymethyl-α-D-glucopyranosyl-(1→4)-O-α-D-glucopyranosyl-(1→4)-O-α-D-glucopyranosyl-(1→4)-O-α-D-glucopyranosyl-(1→4)-O-α-D-glucopyranosyl-(1→4)-D-[1-(o-methoxyphenoxy)-glucopyranose] synthesized according to Synthesis Example 2, 20 mmole of HEPES (N-2-hydroxyethyl-piperidine-N'-2-ethanesulfonic acid), 10 mmole of calcium chloride, 40 units of tyrosinase, 500 units of glucoamylase and 3 mg of 4-aminoantipyrine in purified water, and made pH 6.9 with NaOH and a total amount 20 ml with purified water.

[Measuring Procedures]

To 2 ml of Reagent Solution 1, 100 μl of sample serum was added and incubated at 37° C. Increased amount of absorbance of the reaction solution per minute was measured at a wavelength of 505 nm.

Figure 5:
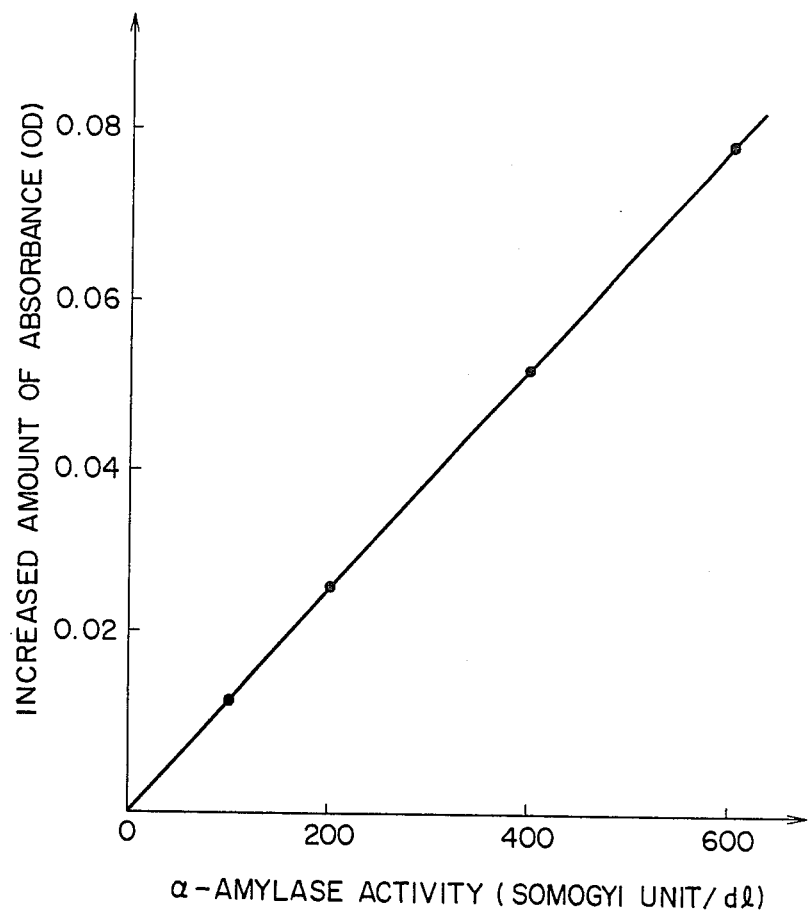

On the other hand, using standard samples of known α-amylase activity, a calibration curve was obtained by the same procedure as mentioned above. From this calibration curve, the α-amylase activity in the sample was obtained. FIG. 5 shows a relationship between the α-amylase activity (Somogyi units/dl) at individual dilution stages of standard samples and the increased amount of absorbance (OD) per minutes at a wavelength of 505 nm.

EXAMPLE 7

[Measuring Reagents]

(1) Reagent Solution 1

In purified water, 30 mmole of PIPES [piperadine-N,N-bis(2-ethanesulfonic acid)] and 10 mmole of calcium chloride were dissolved and pH was made 6.9 with NaOH. The total amount of the solution was made 1 liter with purified water. Then, glucoamylase was dissolved in the solution so as to make the concentration 30 U/ml.

(2) Reagent Solution 2

In 20 ml of Reagent Solution 1, 15 mg of O-6-deoxy-6-[anilino]-α-D-glucopyranosyl-(1→4)-O-α-D-glucopyranoxyl-(1→4)-O-α-D-glucopyranosyl-(1→4)-O-α-D-glycopyranoxyl-(1→4)-O-α-D-glucopyranosyl-(1→4)-D-[1-(4-methylumbelliferyl)-glucopyranose] was dissolved.

(3) Reagent Solution 3

An aqueous solution in an amount of 1 liter with pH 10.5 was prepared by dissolving 0.2 mole of sodium bicarbonate in purified water and adjusting the pH with NaOH.

[Measuring Procedures]

To 2 ml of Reagent Solution 2, 10 μl of sample serum was added and incubated at 37° C. for 5 minutes, followed by addition of 10 ml of Reagent Solution 3. To 2 ml of Reagent Solution 1, 10 μl of sample serum was added, followed by the same procedure as mentioned above to give a reagent blank. Fluorescence intensity (excitation wavelength 365 nm, fluorescence wavelength 450 nm) of each reaction solution was measured. From the fluorescence intensity using Reagent Solution 2, the fluorescence intensity of sample blank using Reagent Solution 1 was substracted.

Figure 6:
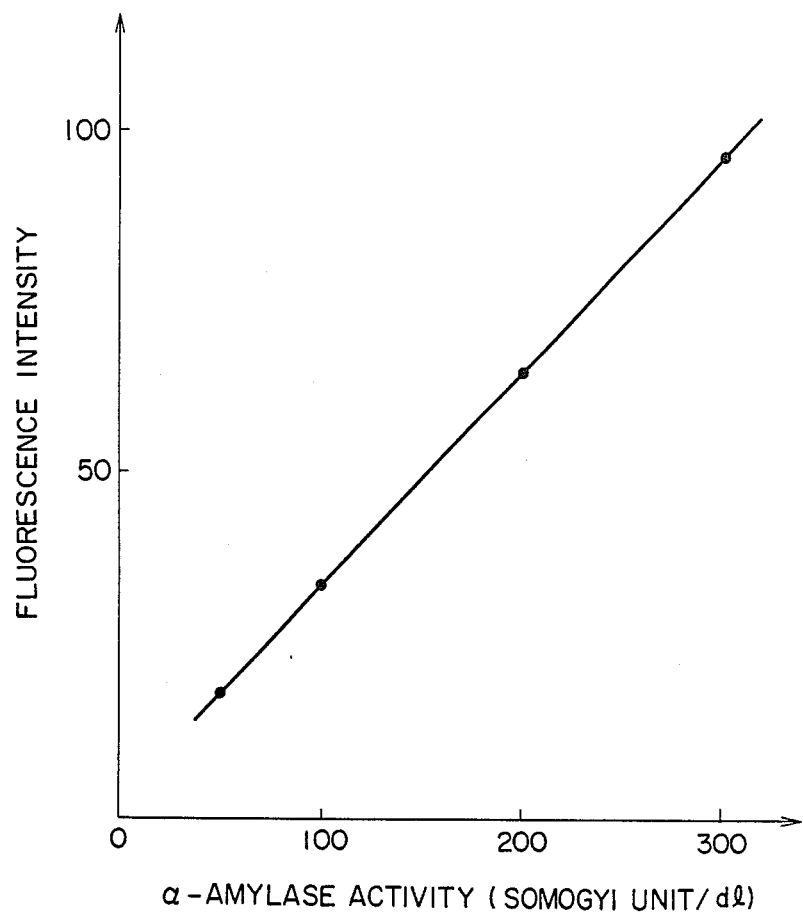
FIG. 6 is a graph showing a calibration curve obtained in Example 7, wherein α-amylase activity (Somogyi unit/dl) is taken along the abscissa axis and a fluorescence intensity is taken along the ordinate axis.

On the other hand, using standard samples of known α-amylase activity, a calibration curve was obtained by the same procedure as mentioned above. From this calibration curve, the α-amylase activity in the sample was obtained. FIG. 6 shows a relationship between the α-amylase activity (Somogyi units/dl) at individual dilution stages of standard samples and the fluorescence intensity.

What is claimed is:

1. An oligosaccharide derivative represented by the formula:

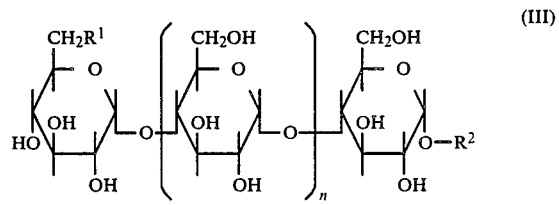

(III)

wherein n is an integer of 2 to 5; $R^1$ is a pyridylamino group, an anilino group, a methylanilino group, a hydroxyanilino group and a carboxyphenylamino group, an alkylamino group wherein the alkyl moiety has 1 to 4 carbon atoms, a carboxymethoxy group or a salt thereof; a $R^2$ is a group of the formula:

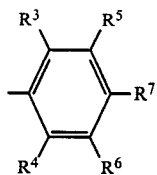

wherein $R^3$ through $R^6$ are independently hydrogen, an alkyl group having 1 to 4 carbon atoms, an alkoxy group having 1 to 4 carbon atoms, a nitro group, a carboxyl group, a sulfone group or a halogen; and $R^7$ is hydrogen, an alkoxy group having 1 to 4 carbon atoms, a halogen or a nitro group, a group of the formula:

(V)

wherein $R^8$ is hydrogen or a methyl group, or a group of the formula:

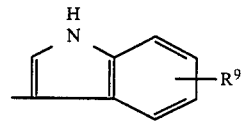

wherein $R^9$ is a hydrogen or a halogen.

2. An oligosaccharide derivative according to claim 1, wherein $R^1$ is a 2-pyridylamino group, a 3-pyridylamino group, an anilino group, a methylanilino group, a hydroxyanilino group, a carboxyphenylamino group or an alkylamino group wherein the alkyl moiety has 1 to 4 carbon atoms.

3. An oligosaccharide derivative according to claim 1, wherein $R^1$ is a carboxylethoxy group or a salt thereof.

4. An oligosaccharide derivative according to claim 1, which is represented by the formula:

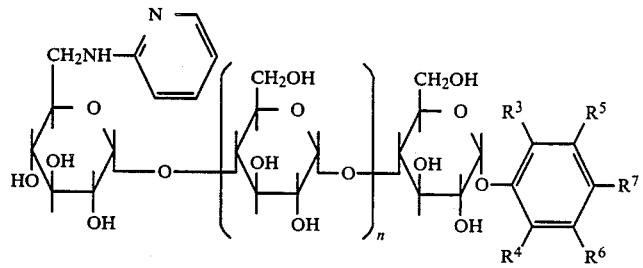

wherein $R^3$ through $R^7$ are independently hydrogen, a halogen or a nitro group; and n is an integer of 2 to 5.

5. An oligosaccharide derivative according to claim 1, which is represented by the formula:

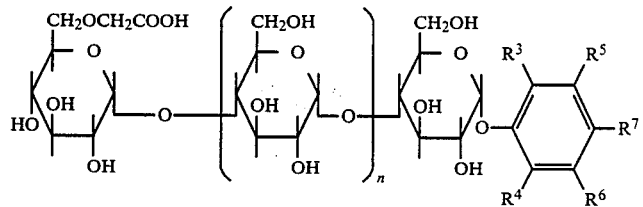

wherein $R^3$ through $R^7$ are independently hydrogen, a halogen or a nitro group; and n is an integer of 2 to 5.

6. An oligosaccharide derivative according to claim 1, which is represented by the formula:

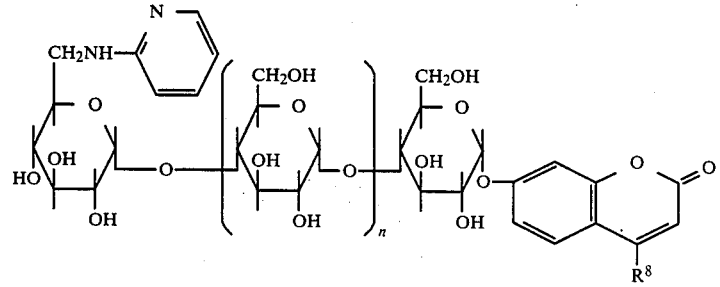

wherein $R^8$ is hydrogen or a methyl group; and n is an integer of 2 to 5.

7. An oligosaccharide derivative according to claim 1, which is represented by the formula:

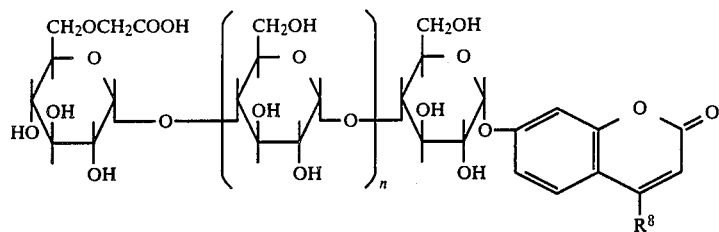

wherein $R^8$ is hydrogen or a methyl group; and n is an integer of 2 to 5.

8. An oligosaccharide derivative according to claim 4, which is

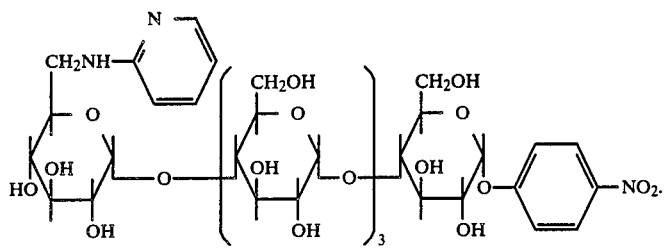

9. An oligosaccharide derivative according to claim 4, which is

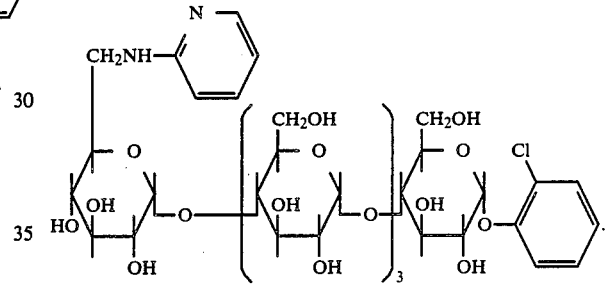

10. An oligosaccharide derivative according to claim 5, which is

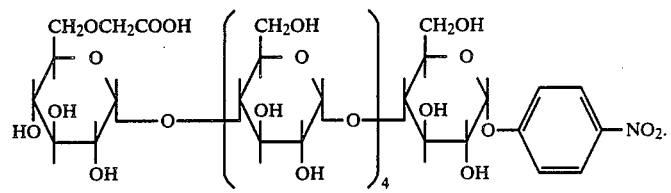

11. An oligosaccharide derivative according to claim 1, which is

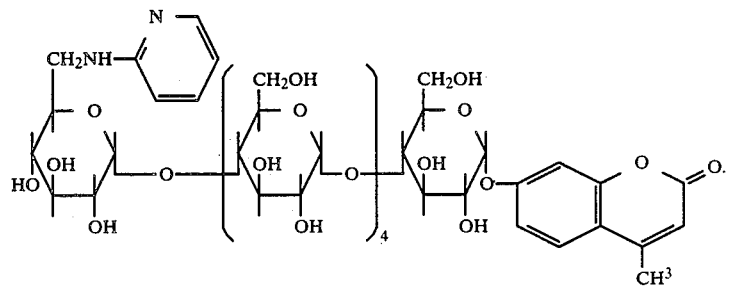

12. An oligosaccharide derivative according to claim 1, which is

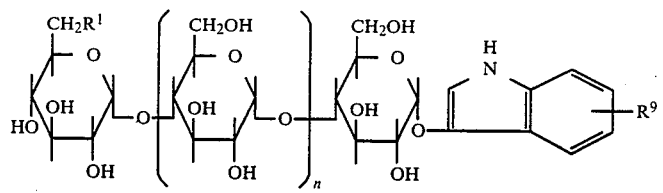
wherein $R^1$ is a carboxymethoxy group or a salt thereof, a 2-pyridylamino group or a 3-pyridylamino group; $R^9$ is hydrogen or a halogen; and n is an integer of 3 to 5.
* * * * *